(12) United States Patent
Song

(10) Patent No.: US 9,585,826 B2
(45) Date of Patent: Mar. 7, 2017

(54) TRIGGERABLE COMPOSITIONS FOR TWO-STAGE, CONTROLLED RELEASE OF ACTIVE CHEMISTRY

(71) Applicant: Kimberly-Clark Worldwide, Inc., Neenah, WI (US)

(72) Inventor: Xuedong Song, Alpharetta, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 653 days.

(21) Appl. No.: 13/671,291

(22) Filed: Nov. 7, 2012

(65) Prior Publication Data

US 2014/0128827 A1    May 8, 2014

(51) Int. Cl.
| | | |
|---|---|---|
| *A61K 8/44* | (2006.01) | |
| *A61L 15/20* | (2006.01) | |
| *A61L 15/46* | (2006.01) | |
| *A61K 8/11* | (2006.01) | |
| *A61Q 19/00* | (2006.01) | |
| *A61L 15/24* | (2006.01) | |
| *A61L 15/44* | (2006.01) | |
| *A61K 8/81* | (2006.01) | |

(52) U.S. Cl.
CPC ............ *A61K 8/44* (2013.01); *A61K 8/11* (2013.01); *A61K 8/8152* (2013.01); *A61K 8/8182* (2013.01); *A61L 15/24* (2013.01); *A61L 15/44* (2013.01); *A61L 15/46* (2013.01); *A61Q 19/005* (2013.01); *A61K 2800/56* (2013.01); *A61L 2300/602* (2013.01); *A61L 2300/62* (2013.01)

(58) Field of Classification Search
None
See application file for complete search history.

(56) References Cited

U.S. PATENT DOCUMENTS

| | | | |
|---|---|---|---|
| 4,020,156 A | 4/1977 | Murray et al. | |
| 4,540,564 A | 9/1985 | Bodor | |
| | (Continued) | | |

FOREIGN PATENT DOCUMENTS

| | | |
|---|---|---|
| EP | 0752465 A1 | 1/1997 |
| EP | 0771785 B1 | 1/2002 |
| | (Continued) | |

OTHER PUBLICATIONS

Co-pending U.S. Appl. No. 13/230,102, filed Sep. 12, 2011, by Song et al. for "Wetness Indicator Having Varied Hues."

(Continued)

*Primary Examiner* — Jeffrey Washville
(74) *Attorney, Agent, or Firm* — Kimberly-Clark Worldwide, Inc.

(57) ABSTRACT

A triggerable composition for two-stage, controlled release of a functional active chemical includes an encapsulation material for encapsulating a betaine ester or betaine ester derivative including a functional active. The encapsulation material is triggerable to release the betaine ester or betaine ester derivative at a first stage upon the occurrence with an environmental stimulus, such as a pH change, an enzymatic change, and a temperature change. The betaine ester or betaine ester derivative of a functional active with at least one hydroxyl group releases the functional active through a hydrolysis reaction upon contact with an aqueous medium.

20 Claims, 5 Drawing Sheets

(56) References Cited

U.S. PATENT DOCUMENTS

| | | | |
|---|---|---|---|
| 4,880,921 A | 11/1989 | Bodor | |
| 5,130,290 A | 7/1992 | Tanimoto | |
| 5,133,958 A | 7/1992 | Stuckler | |
| 5,197,958 A | 3/1993 | Howell | |
| 5,389,093 A | 2/1995 | Howell | |
| 5,622,944 A | 4/1997 | Hale et al. | |
| 5,827,913 A | 10/1998 | Baetzold et al. | |
| 5,958,870 A * | 9/1999 | Declercq et al. | 510/504 |
| 6,369,290 B1 | 4/2002 | Glaug et al. | |
| 6,458,456 B1 | 10/2002 | Zainiev et al. | |
| 6,586,639 B2 | 7/2003 | Murayama et al. | |
| 6,677,297 B2 | 1/2004 | Frerot | |
| 7,056,878 B2 | 6/2006 | Fender et al. | |
| 7,105,715 B2 | 9/2006 | Carlucci et al. | |
| 7,229,958 B2 | 6/2007 | Koehle et al. | |
| 7,294,612 B2 | 11/2007 | Popplewell et al. | |
| 7,407,670 B2 | 8/2008 | Six et al. | |
| 7,501,536 B2 | 3/2009 | Jaunky et al. | |
| 7,550,416 B2 | 6/2009 | Woo et al. | |
| 7,655,830 B2 | 2/2010 | Flohr et al. | |
| 7,758,888 B2 | 7/2010 | Lapidot et al. | |
| 8,022,030 B2 | 9/2011 | Berthier et al. | |
| 2003/0083513 A1 | 5/2003 | Murayama et al. | |
| 2004/0110891 A1 | 6/2004 | Guo et al. | |
| 2004/0234597 A1 | 11/2004 | Shefer et al. | |
| 2005/0131363 A1 | 6/2005 | Kim et al. | |
| 2007/0021319 A1 | 1/2007 | Kohle et al. | |
| 2007/0031485 A1 | 2/2007 | Ljusberg-Wahren et al. | |
| 2007/0081953 A1 | 4/2007 | Dahms | |
| 2007/0105793 A1 | 5/2007 | Hendrix | |
| 2007/0160553 A1 | 7/2007 | Kripp et al. | |
| 2007/0270773 A1 | 11/2007 | Mackey | |
| 2007/0281007 A1 | 12/2007 | Jacob et al. | |
| 2008/0139378 A1 * | 6/2008 | Hildebrand et al. | 502/1 |
| 2008/0221173 A1 | 9/2008 | Bhaskaran et al. | |
| 2008/0279253 A1 | 11/2008 | MacDonald et al. | |
| 2008/0286224 A1 | 11/2008 | Vega et al. | |
| 2009/0054860 A1 | 2/2009 | Young et al. | |
| 2009/0156634 A1 | 6/2009 | Molino et al. | |
| 2009/0221980 A1 * | 9/2009 | Mosbacher et al. | 604/385.01 |
| 2009/0275906 A1 * | 11/2009 | Berland et al. | 604/359 |
| 2009/0275908 A1 | 11/2009 | Song | |
| 2010/0012017 A1 | 1/2010 | Miller | |
| 2010/0030173 A1 | 2/2010 | Song et al. | |
| 2010/0160299 A1 | 6/2010 | Baker, Jr. et al. | |
| 2010/0221330 A1 | 9/2010 | Messadek | |
| 2010/0227896 A1 | 9/2010 | Biedermann et al. | |
| 2010/0248959 A1 | 9/2010 | Kato et al. | |
| 2010/0307422 A1 | 12/2010 | Huck et al. | |
| 2011/0015599 A1 | 1/2011 | Song et al. | |
| 2011/0046571 A1 | 2/2011 | Waldhorn | |
| 2011/0104023 A1 | 5/2011 | Nakatsubo et al. | |
| 2011/0144603 A1 | 6/2011 | Song | |
| 2011/0152805 A1 | 6/2011 | Gil | |
| 2011/0250286 A1 | 10/2011 | Marcello et al. | |
| 2012/0064136 A1 | 3/2012 | Baker, Jr. et al. | |
| 2012/0121669 A1 | 5/2012 | Fontana et al. | |
| 2012/0259098 A1 | 10/2012 | Baker, Jr. et al. | |
| 2013/0018076 A1 | 1/2013 | Friedel et al. | |

FOREIGN PATENT DOCUMENTS

| | | |
|---|---|---|
| JP | 01-275511 A | 11/1989 |
| JP | 03-221039 A | 9/1991 |
| WO | WO 98/26808 A2 | 6/1998 |
| WO | WO 01/27234 A1 | 4/2001 |
| WO | WO 03/047558 A2 | 6/2003 |
| WO | WO 2008/068059 A2 | 6/2008 |
| WO | WO 2009/018368 A1 | 2/2009 |
| WO | WO 2010/088053 A2 | 8/2010 |
| WO | WO 2012/094636 A2 | 7/2012 |
| WO | WO 2013/016257 A1 | 1/2013 |
| WO | WO 2013/070674 A1 | 5/2013 |

OTHER PUBLICATIONS

Co-pending U.S. Appl. No. 13/292,612, filed Nov. 9, 2011, by Wei et al. for "Non-Tacky Wetness Indicator Composition for Application on a Polymeric Substrate."

Huh, Kang Moo et al., "pH-Sensitive Polymers for Drug Delivery," Macromolecular Research, vol. 20, No. 3, Mar. 2012, pp. 224-233.

Balamuralidhara, V. et al., "pH-Sensitive Drug Delivery Systems: A Review," American Journal of Drug Discovery and Development, vol. 1, No. 1, 2011, pp. 24-48.

* cited by examiner

TRIGGERABLE COMPOSITIONS FOR TWO-STAGE, CONTROLLED RELEASE OF ACTIVE CHEMISTRY

FIELD OF INVENTION

The present invention pertains to a composition which controls the chemical release of functionally active components from a previously inactive and protected state. In particular, the present invention pertains to a composition which gradually or rapidly release active chemical components upon the occurrence of specific environmental stimuli, the composition for use in bandages, hygiene products, health care products and skin-contacting beauty products, as well as in consumer product applications. The present invention also relates to such bandages, hygiene products, health care products, beauty products and consumer products incorporating such chemistry.

BACKGROUND

A large number of functionally active chemicals are known for use with personal care and beauty products, hygiene products, health-care related products, and skin-contacting products. For example, such actives include antimicrobial or antibacterial agents, antioxidant agents, antiseptic-type agents skin repairing agents, and fragrances. Unfortunately, many of these functionally active chemicals are not stable under various environmental conditions. For example, if such actives include volatile components, such as those found in fragrances they may dissipate into the surrounding environment upon exposure to air and humidity conditions. Therefore such chemicals may demonstrate short shelf lives when in use, and present serious packaging/storage concerns. As a result, costly packaging requirements may be necessary for products incorporating such chemicals. This instability therefore creates a significant limitation on the wide adoption of the potentially useful chemistry, and limits the long-term efficacy of products incorporating such chemistry. Further, processing challenges such as elevated temperatures may exist, and as a result, may present a need to limit exposure to environmental stimuli during manufacture.

Additional challenges that use of such active chemicals presents include the difficulties involved with gradually controlling the release of such active chemicals, as well as the potential side effects/costs resulting from use of chemically degraded products. Other actives, such as antioxidants, are also often not stable when exposed to ambient conditions, such as the air of a user's pantry or storage closets. Antioxidants can readily be oxidized by oxygen in the air. Some skin repairing chemicals are also not stable when exposed to the surrounding environment. For example, the skin repairing agent retinol is not stable under ambient conditions without protection from the environment. In fact, it can become a skin irritant when its concentration is relatively high. A need therefore exists for a versatile composition that effectively stabilizes functional chemical actives, and releases such actives upon demand at a desirable rate and profile.

Certainly, attempts have been made to overcome the stability and storage limitations presented by such actives. For example, attempts have been suggested for stabilizing retinol by encapsulating it in pH sensitive polymers and then releasing it at a later time by changing the solubility of the encapsulating matrix through a pH change. The encapsulated retinol still suffers significant degradation, presumably from oxidation. Others have suggested in order to overcome such stability issues, to convert retinol into an ester as a proactive (a precursor to the retinol active) and then at a later time, to convert the ester into the active form by use of enzymes present in a user's body after delivery through a user's skin. However, with such methodology, only a small portion of the ester is used effectively by the skin layer and a majority of the esters are wasted by the system. Such a system may also actually lead to side effects when too much retinol ester is used to achieve effective dosages on the skin. Therefore, a need still exists for delivery compositions for skin repair actives.

In connection with the delivery of fragrances (such as in connect on with personal care absorbent products), it has been suggested to encapsulate fragrances in polymeric matrices for stabilization and delivery benefits. However, even with such encapsulation technology, there is a further need for fragrance encapsulation technology for use in consumer products which offers effective protection for such volatiles as well as a controlled release. Existing encapsulation chemistries for consumer products often leak or release prematurely. Therefore a continuing need exists for a material composition that both provides stability for unstable actives, and which also provides for release of actives in a controlled manner.

SUMMARY OF THE INVENTION

The current invention is directed to a triggerable composition for creating a stable, controlled-release of functional chemical active components using a two-stage release mechanism. The graduated or rapid release of functional chemical active components allows for protection of the functional actives from the surrounding environment, as well as the selective release of such actives, upon the occurrence of two select environmental stimuli. The protection and stabilization of the functional active is accomplished through esterification of the functional active into a betaine ester molecule, as well as the incorporation of the modified betaine ester molecule, into an encapsulation polymer matrix. Subsequent triggered release of the functional active from the betaine ester molecule is dependent upon preselected properties of the encapsulation polymer matrix (first stage trigger), as well as the hydrolysis of the betaine ester (by an aqueous medium in a second stage trigger), once the betaine ester molecule is released or freed from the encapsulation polymer matrix. For the purposes of this application, the term "aqueous medium" shall mean a medium containing "liquid" water as opposed to water vapor. Such aqueous medium is exemplified by urine, sweat, vaginal fluids, mucous, menses, and runny, liquid, and loose bowel movements.

The functional active chemicals can be a fragrance, a skin repairing agent, an antioxidant agent, an antimicrobial/antibacterial agent an antifungal agent, a hormone, and a medically active agent. Stabilization of the functional active chemicals through a betaine ester molecule and within an encapsulation polymer matrix, prevents the premature release of the chemicals into either the environment or to a desired location. The functional active chemicals can be derived from substances including at least one hydroxyl group that are volatile, water-sensitive, or easily oxidized by oxygen. The stabilization is specifically accomplished by the incorporation of a radical form of the functional active chemicals into the betaine ester, of the general formula $R_3R_4R_5N-R_2R_1COOR$ $X-$. The ester bond connecting the radical (R) of the functional active to the betaine portion of the molecule in the betaine ester, can be readily hydrolyzed upon exposure to an aqueous medium to release the active. The encapsulation polymer matrix protecting the betaine ester can be designed to be sensitive to water in either a neutral, acidic or basic condition, or alternatively, to be sensitive to enzymes, ions, or ligands.

In one embodiment of the invention, a triggerable composition for two-stage, controlled release of a functional active chemical includes a betaine ester or betaine ester derivative of a functional active with at least one hydroxyl group that releases the functional active through a hydrolysis reaction upon contact with an aqueous medium, and an encapsulation material for encapsulating the betaine ester or betaine ester derivative including a functional active, the encapsulation material triggerable to release the betaine ester or betaine ester derivative upon the occurrence of an environmental stimulus.

In an alternative embodiment of the invention, the triggerable composition includes an encapsulation material that is triggerable upon the occurrence of an environmental stimulus that is selected from the group consisting of a pH change, an enzymatic change, a temperature change, an ion concentration change, and a ligand concentration change. Desirably in one embodiment, such encapsulation material is triggerable upon the occurrence of an environmental stimulus that is selected from the group consisting of a pH change, an enzymatic change and a temperature change. Desirably in a further embodiment, the encapsulation material is triggerable to release a betaine ester or betaine ester derivative upon the occurrence of a pH change in the surrounding environment. In a further alternative embodiment, the composition including the encapsulation material and betaine ester or betaine ester derivative, is in the form of particles, microparticles, nanoparticles, fibers, sheets, films or combinations thereof.

In yet another alternative embodiment of the invention, the triggerable composition includes an encapsulation material that is selected from copolymers of methacrylic acid and methyl methacrylate which are sensitive to basic aqueous solutions, copolymers of dimethylaminoethyl methacrylate, butyl methacrylate, and methyl methacrylate which are sensitive to acidic aqueous solutions, and vinyl pyrrolidone/vinyl acetate copolymers which are sensitive to neutral aqueous solutions.

In still another alternative embodiment of the invention, the triggerable composition includes a functional active on the betaine ester or betaine ester derivative, which functional active is selected from the group consisting of a fragrance, an antimicrobial agent, an antioxidant agent, a skin repairing agent, an antifungal agent, a hormone, and a medically active agent. In yet another alternative embodiment of the invention, the functional active is a fragrance including at least one hydroxyl group, selected from the group of fragrances consisting of thymol, eugenol, menthol and vanillin. In a desirable alternative embodiment, the functional active is a ski n-repairing agent. In a further alternative embodiment, the ski n-repairing agent is derived from retinol.

In another alternative embodiment of the invention, an absorbent article includes at least one absorbent layer, and the absorbent article further includes the triggerable composition of the invention. In a further alternative embodiment of the invention, an absorbent article including the inventive triggerable composition includes a topsheet layer, a backsheet layer, and at least one absorbent core layer, wherein the triggerable composition is included with at least one of the topsheet layer, absorbent core layer and said backsheet layer of the absorbent article. In a further alternative embodiment of the invention involving an absorbent article, the triggerable composition is included with a carrier layer for carrying the triggerable composition within the absorbent article. In yet another alternative embodiment of the invention, the absorbent article which is coated or treated with the triggerable composition, is selected from the group consisting of feminine care hygiene articles, adult incontinence articles, baby and child care articles, bandages, medical garments and in treatment sheets. In still a further alternative embodiment of the invention, the triggerable composition of the invention is a part of a lotion, cream or medicament.

In another embodiment of the invention, a triggerable composition for two-stage, control led release of a functional active chemicals includes a betaine ester or betaine ester derivative for release of a functional active contained on the betaine ester or betaine ester derivative, through a hydrolysis reaction upon contact with an aqueous medium, and an encapsulation material for encapsulating the betaine ester or betaine ester derivative including a functional active. The encapsulation material is triggerable to release the betaine ester or betaine ester derivative upon the occurrence of an environmental stimulus, wherein the environmental stimulus is a pH change. In another alternative embodiment of the invention, the composition is triggerable upon an environmental stimulus that is a pH change from an acidic to neutral or basic environment, and such encapsulation material is selected from the group consisting of copolymers of methacrylic acid and methyl methacrylate which are sensitive to basic aqueous solutions, and vinyl pyrrolidone/vinyl acetate copolymers which are sensitive to neutral aqueous solutions. In an alternative embodiment, the composition is triggerable upon an environmental stimulus that is a pH change from a basic to neutral or acidic environment, and the encapsulation material is selected from the group consisting of copolymers of dimethyl aminoethyl methacrylate, butyl methacrylate, and methyl methacrylate which are sensitive to acidic aqueous solutions, and vinyl pyrrolidone/vinyl acetate copolymers which are sensitive to neutral aqueous solutions. In yet another alternative embodiment, such a composition includes a functional active that is a fragrance. In another alternative embodiment such fragrance is selected from thymol, menthol and eugenol.

Other features and aspects of the present disclosure are discussed in greater detail below.

DETAILED DESCRIPTION OF THE INVENTION

Figure 1:
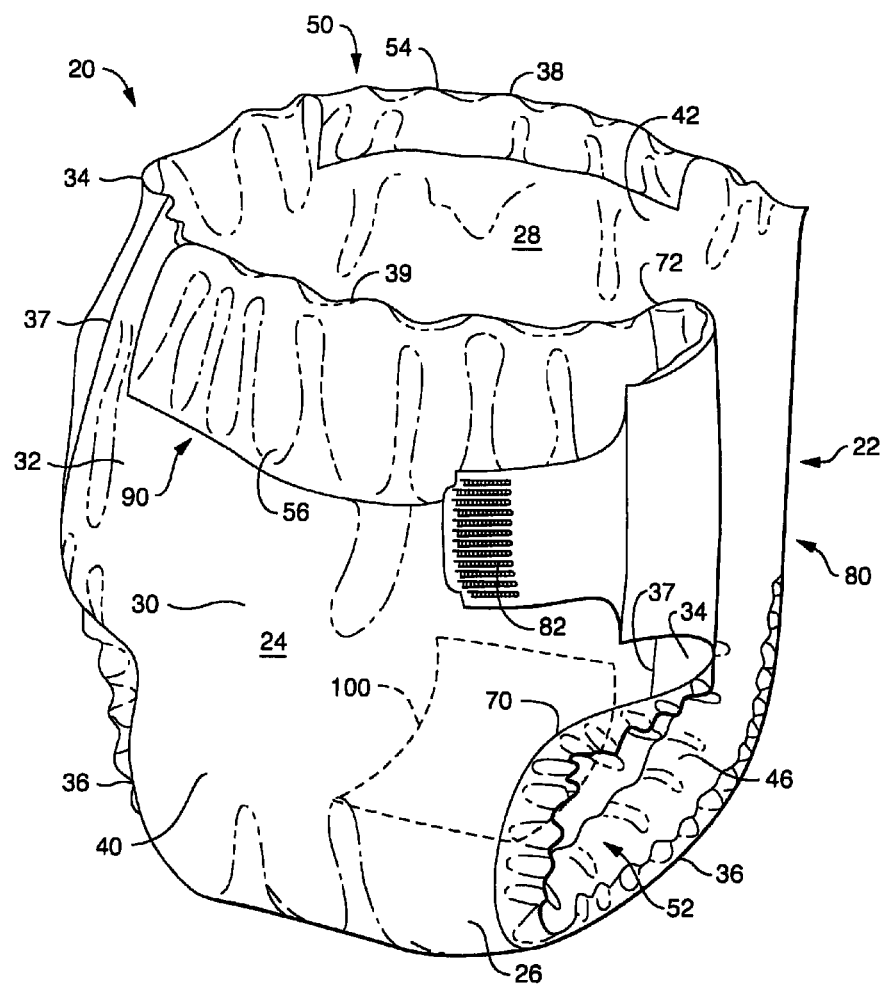
FIG. 1 is a rear perspective view of an embodiment of a personal care absorbent article having a chemical composition coating according to the invention, the article in the form of an unfastened diaper.

In general, the present invention is directed to a composition that includes an encapsulation chemistry for selectively releasing a functional active through a betaine ester or betaine ester derivative and stimuli-sensitive encapsulation chemistries. The selective triggering of the encapsulation chemistries will expose the betaine ester or betaine ester derivative to an aqueous medium. In a second stage, upon exposure of the betaine ester or betaine ester derivative to the aqueous medium, a hydrolysis reaction will occur, resulting in the release of the functional active from the betaine ester or betaine ester derivative into the surrounding environment or at a targeted location. The surrounding environment or targeted location may be onto a user's skin, or into the structure of an article containing the triggerable composition. Such article may be for example, a health care product, such as a garment or bandage, a hygiene product such as a tissue or wipe, a skin-contacting beauty product such as a facial wrap, an absorbent consumer/personal care article, such as a feminine care pad or liner, a baby or child care diaper, or an adult incontinence garment. The composition of the invention may further be present in a lotion, cream or medicament as well.

Betaine Esters of Betaine Ester Derivatives

The functional active chemistry of the composition may be a fragrance, an antioxidant, an antimicrobial or antibacterial agent, or a skin repairing agent. The functional active has a hydroxyl group in its molecular structure. The functional active chemicals are converted into a betaine ester or betaine ester derivative. The rationale for converting the active (ROH chemical) into an ester form of betaine is to modify the properties of the active. There are several properties of actives that can be modified by this structural change, such as volatility (and consequential difficulty in storage, handling and processing). The ester form of the active would be nonvolatile. The property of oxidation can also be controlled by conversion of a material into the betaine ester form. Antioxidants and skin-repair agents (such as retinol) can also be placed in a more stable form when converted into a betaine ester. Further, some actives demonstrate poor solubility (such as thymol) which has low bioavailability. The betaine ester forms can improve water solubility of these actives. Some actives demonstrate poor permeability (such as retinol) through biological barriers such as skin cells. The betaine ester form of such actives can be used to balance the hydrophilicity/hydrophobicity of the active to improve skin permeability. The betaine ester form can also be used to control the release rate of an active.

For the purposes of this description, a suitable betaine ester shall be described by the general formula of:

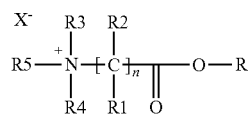

The betaine ester is an ester of betaine and the functional active chemistry with one or more hydroxyl groups. That is, the (R) group is a radical of the functional active, such as the radical of a volatile fragrance alcohol with one or more hydroxyl groups. Desirably in one embodiment, the (R) moiety is independently derived from a fragrance alcohol of more than four (4) carbon atoms of synthetic or natural origin; each R1, R2, R3, R4 and R5 independently is selected from hydrogen, or organic moieties such as alkyl, hydroxyalkyl, aryl, or aromatic groups, with $n \geq 1$, preferably 2 or 3, and $\leq 4$, because the larger the number "n", the less likelihood of rapid hydrolysis (hence the slower the release of fragrance). Desirably in one embodiment, groups R3-R5 include less than 8-carbon atoms in totality, desirably with any one group (R3, R4 or R5) including between 2-6 carbon atoms. In one embodiment, each R3-R5 group is desirably a methyl group. X is a compatible anion.

The (R) group includes components having the desired functionality. For example, if such (R) group is a fragrance alcohol group component it includes components having odiferous properties. It should also be recognized that the larger the value for "n", the more difficult also for the betaine este to solubilize in water as well as undergo hydrolysis. Further, the smaller the R1 thru R5 groups, the less stable the betaine ester with associated (R) group is, in the sense that the more likelihood that vapor/humidity in the air alone will cause the disassociation of the (R) group (such as fragrance alcohol) from the betaine ester molecule. Further, if the betaine ester is too hydrophobic, that is, if it includes large hydrophobic groups in the R3-R5 positions, or is part of a larger hydrophobic structure, the more likely that it will not be water soluble, or less so. The (R) group may include radicals of nonfragrance functional components, such as retinol, which is attached at the ester linkage.

As noted, it is desirable that the betaine ester is not large, (not including an "n" number larger than 4, that it is not part of a larger polymer structure, and not itself bonded as a functional group, to a chain base structure) such that it can be easily solubilized, and not be so hydrophobic in nature that it would be difficult to process, and would impact aqueous liquid flow on a coated absorbent substrate. Further, if the betaine ester is too large, in that it includes larger groups in its R3-R5 positions, or is part of a larger structure, it has been found that the hydrolysis reaction time is slower. In a desirable embodiment, such betaine ester includes only hydrogen or alkyl carbon-based moieties in its R1-R5 groups.

In one embodiment, the functional active (radical of the fragrance alcohol embodiment) of the (R) group is selected from the fragrance group comprising 4-allyl-2-methoxyphenol (eugenol), 3-(2-bornyloxy)-2-methyl-1-propanol, 2-tert-butylcyclohexanol, 4-tert-butylcyclohexanol, benzyl alcohol, 1-decanol, 9-decen-1-ol, dihydroterpineol, 2,4-dimethyl-4-cyclohexen-1-yl methanol, 2,4-dimethyl cyclohexyl methanol, 2,6-dimethyl-2-heptanol, 2,6-dimethyl-4-heptanol, 3a,4,5,6,7,7a-hexa hydro-2,4-dimethyl-4,7-methano[1H]inden-5-ol, 3,7-dimethyl-1,6-nonadien-3-ol, 2,6-dimethyl-2,7-octadien-6-ol (linalool), cis-3,7-dimethyl-2,6-octadien-1-ol (nerol), trans-3,7-dimethyl-2,6-octadien-1-ol (geraniol), 3,7-dimethyl-1,7-octanediol, 3,7-dimethyl-1-octanol (tetra hydrogeraniol), 2,6-dimethyl-2-octanol (tetra hydromyrcenol), 3,7-dimethyl-3-octanol (tetra hydrolinalool), 2,6-dimethyl-7-octen-2-ol (dihydromyrcenol), 3,7-dimethyl-6-octen-1-ol (citronellol), 2,2-dimethyl-3-(3-methyl phenyl)-1-propanol, 2,2-dimethyl-3-phenyl-1-propanol, 2-ethoxy-4-methoxymethyl phenol, 2-ethyl-4-(2,2,3-trimethyl-3-cyclopenten-1-yl)-2-buten-1-ol, cis-3-hexen-1-ol, 4-(4-hydroxy-3-methoxyphenyl)-2-butanone, 1-hydroxy-2-(1-methyl-1-1 hydroxyethyl)-5-methyl cyclohexane, 3-(hydroxymethyl)-nonanone, 4-(4-hydroxy-4- methyl pentyl)-3-cyclohexene-1-carboxaldehyde, isoborneol, 3-isocamphylcyclohexanol, 2-isopropenyl-5-methylcyclohexanol (isopulegol), 1-isopropyl-4-methylcyclohex-3-enol (terpinenol), 4-isopropylcyclohexanol, 1-(4-isopropylcyclohexyl) ethanol, 4-isopropylcyclohexylmethanol, 2-isopropyl-5-methylcyclohexanol (menthol), 2-isopropyl-5-methyl phenol (thymol), 5-isopropyl-2-methyl phenol (carvacrol), 2-(4-methyl-3-cyclohexenyl)-2-propanol (terpineol), 2-(4-methylcyclohexyl)-2-propanol (dihydroterpineol), 4-methoxybenzyl alcohol, 2-methoxy-4-methyl phenol, 3-methoxy-5-methyl phenol, 1-methoxy-4-propenyl benzene (anethol), 2-methoxy-4-propenyl phenol (isoeugerol), 4-methyl-3-decen-5-ol, 2-methyl-6-methylene-7-octen-2-ol (myrcenol), 3-methyl-4-phenyl-2-butanol, 2-(2-methyl phenyl)ethanol, 2-methyl-4-phenyl-1-pentanol, 3-methyl-5-phenyl-1-pentanol, 2-methyl-1-phenyl-2-propanol, (1-methyl-2-(1,2,2-trimethylbicyclo[3.1.0]hex-3-ylmethyl)cyclopropyl)methanol, 3-methyl-4-(2,2,6-trimethylcyclohexen-1-yl)-2-butanol, 2-methyl-4-(2,2,3-trimethyl-3-cyclopenten-1-yl)-2-buten-1-ol, (3-methyl-1-(2,2,3-trimethyl-3-cyclopentenyl)-3-cyclohexen-1-yl)methanol, 3-methyl-5-(2,2,3-trimethyl-3-cyclopenten-1-yl)-4-penten-2-ol, 2-methyl-2-vinyl-5-(1-hydroxy-1-methylethyl) tetrahydrofuran, trans, cis-2,6-nonadienol, 1-nonanol, nopol, 1,2,3,4,4a,5,6,7-octa hydro-2,5,5-trimethyl-2-naphthol, 1-octanol, 3,4,5,6,6-pentamethyl-2-heptanol, 2-phenyl ethanol, 2-phenylpropanol, 3-phenylpropanol (hydrocinnamic alcohol), 3-phenyl-2-propen-1-ol (cinnamic alcohol), 4-(5,5,6-trimethylbicyclo[2.2.1]hept-2-yl)cyclohexan-1-ol, 3,5,5-trimethylcyclohexanol, 2,4,6-trimethyl-4-cyclohexen-1-yl methanol, 5-(2,2,3-trimethyl-3-cyclopentenyl)-3-methyl pentan-2-ol, 3,7,11-trimethyl-2,6,10-dodecatrien-1-ol (farnesol), 3,7,11-trimethyl-1,6,10-dodecatrien-3-ol (nerol idol), 3,5,5-trimethyl-1-hexanol (isononanol), 1-undecanol, 10-undecen-1-ol, vetiverol.

In another desirable embodiment, the fragrance active group (R) on the betaine ester is derived from 2-phenoxyethanol, phenylethyl alcohol, geraniol, citronellol, 3-methyl-5-phenyl-1-pentanol, 2,4-dimethyl-3-cyclohexene-1-methanol, linalool, tetrahydrolinalool, 1,2-dihydromyrcenol, hydroxycitronellal, farnesol, menthol, eugenol, thymol, vanillin, cis-3-hexenol, terpineol and mixtures thereof.

An example of a particularly desirable fragrance active (R) group which is attached to the betaine ester is the radical of eugenol. Eugenol itself is represented by the following formula:

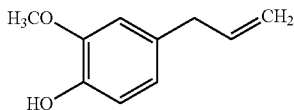

Other particularly desirable (R) groups from volatile fragrance alcohols include, radicals of menthol and thymol, with thymol offering the additional advantage of providing potential anti bacterial functionality to the absorbent article or other article on which it is coated, or lotion, cream or medicament composition in which it is present.

While such fragrance volatiles are actively volatile in their disassociated alcohol state, such volatility is eliminated once their radicals are attached as part of the betaine ester at the (R) location. The relative hydrophobicity and hydrophilicity of the R3-R5 groups can be easily adjusted to tailor the hydrolysis rate upon exposure to aqueous medium, and therefore the release rate of the active ROH. The betaine esters (where desirably R3-R5 are methyl groups and X— is Cl) of menthol and thymol have been found to be hydrolyzed rapidly upon exposure to liquid water under ambient conditions. However, the betaine ester derivatives (where R3 is C8H17, and R4-R5 are methyl groups) of menthol and thymol have been found to be hydrolyzed at a much slower rate under the same conditions.

The "X" anions have no caustic or markedly irritating effect on human or animal ski n, and are desirable for use in the composition, coating, or lotion/cream/medicament formulation for association with the betaine ester. The anions are desirably chosen from the group comprising chloride, bromide, methyl sulfate, ethyl sulfate, sulfate, nitrate, phosphate and hydrogen phosphate.

As noted, once the betaine ester with attached functional active (such as fragrance radical moiety) has been synthesized, it has been found that the (R) group is not volatile and is stable in the absence of an aqueous medium. This is especially the case for betaine esters in which R3-R5 include at least 8 carbons in total, in their structures. Following the introduction of the betaine ester or betaine ester derivative to an aqueous medium, it undergoes a hydrolysis reaction in which the fragrance separates from the betaine ester and is released as an active fragrance volatile. Such is illustrated by the following reaction:

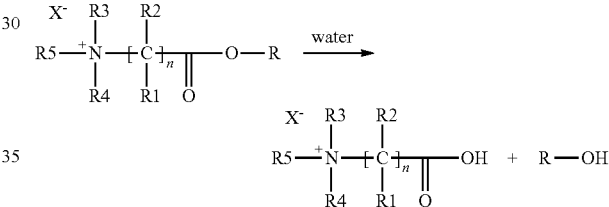

The resulting byproducts are carboxylic acid and an active alcohol or volatile fragrance alcohol ((R—OH) structure), with the latter released into the article or surrounding environment to produce an effect or smell.

In general, betaine esters their derivatives, and their preparation are known, and as such, the synthesis steps of particular betaine esters with radical groups (such as fragrance radicals) will not be further delineated. However, examples of relatively smaller betaine ester molecules with attached fragrance radicals (radical groups of volatile alcohols) may be found in U.S. Pat. No. 5,958,870 to Declercq et al. and EP0752465 to Struillou, each of which are hereby incorporated by reference thereto in their entirety. It has now been found however, that such chemistry is particularly well suited as a base chemistry for an active delivery formulation on various substrates and absorbent articles and in various formulations, particularly if such betaine esters, are limited in size, do not severely impact absorbency pathways either as a result of their level of hydrophobicity or particular placement on a substrate or within an absorbent article.

Desirably, in one embodiment, the betaine ester or betaine ester derivative with attached chemical active, is present in the composition (such as coating) in an amount of between about 0.1 and 30% by weight, alternatively, between about 0.5 to about 15 weight %, further alternatively, between about 1 to 10 weight %. The weight percentages given for this, and further composition components are based on the total weight of the dried composition. It should be recognized that some compositions of the invention will initially utilize organic solvents for initial application of the composition to substrates, although such solvents are contemplated as being dried off during manufacture. Further, it is contemplated that such compositions may also be applied to substrates as hot melted coatings.

Encapsulation Chemistry

As a result of the moisture/aqueous media sensitivity of certain betaine esters as noted above, for those betaine esters with hydrogen or lower alkyl R1-R5 groups, it may be desirable to insulate the betaine ester from moisture and aqueous medium before use so as to delay release of functional active chemicals from hydrolysis. This delay of functional active release can be accomplished by encapsulating the betaine ester in an encapsulating polymer matrix. The encapsulating matrix can be either dissolved/degraded by aqueous media or alternatively, can be swollen by water to expose the betaine esters to water for hydrolysis under various conditions.

The encapsulation chemistry of the inventive composition desirably is triggerable by the occurrence of one or more stimuli to free up the betaine ester or betaine ester derivative protected by the encapsulation chemistry. Such encapsulation chemistry (encapsulation polymer matrix) may be in the form of a continuous cover of polymer/particles, microparticles, nanoparticles, encapsulation polymer coating sheets, films, fibers, laminates, foams, pastes, tablets or suppositories. In such an instance, encapsulating polymers can act as the encapsulation matrix in which the betaine esters or betaine ester derivatives are embedded throughout the whole polymer matrix. Alternatively, such encapsulation chemistry may be a shell of a core/shell configuration, such that an encapsulating polymer shell surrounds the betaine ester or betaine ester derivative core. Such encapsulation chemistry desirably is triggered by pH changes in the environment, but may also be triggered by enzymatic changes, solubility change, changes in temperature via thermogels, changes in ionic concentration and changes in ligand chemistry.

There are a number of polymers that can used to achieve this protection through encapsulation of the betaine esters and derivatives of betaine esters. For example, in one embodiment, dextrans and derivatives can be blended with betaine esters or betaine ester derivatives to form films. Upon contact with an aqueous medium, the dextran and derivatives may be dissolved and the betaine ester then exposed to water for hydrolysis, thereby releasing the functional active.

Environmentally triggerable encapsulation materials, that are triggerable upon specific environmental stimuli, may include copolymers of methacrylic acid and methyl methacrylate, which are sensitive to basic aqueous solutions. Such materials are available under the trade designations EUDRAGIT S-100, L-100 available from Degussa. Alternatively, a copolymer based on dimethylaminoethyl methacrylate, butyl methacrylate, and methyl methacrylate which is sensitive to acidic aqueous solutions may be used. Such materials are available under the trade designation EUDRAGIT E-100 for example, from Degussa. Further encapsulation materials may include vinyl pyrrolidone/vinyl acetate copolymers which are sensitive to neutral aqueous solutions. For example, such are available under the trade designations PVP/VA I-335 from Ashland/ISP.

Certain polymers, such as copolymers of methacrylic acid and methyl methacrylate, which are sensitive to basic aqueous solutions, are particularly effective encapsulation chemistry for use with betaine esters of thymol, menthol and eugenol, in order to minimize water sensitivity and solubility under certain pH. For example, when such betaine ester and polymer films are exposed to neutral water, little menthol, thymol or eugenol is released. However, upon exposure to alkaline aqueous solutions (such as of pH 9), such actives are steadily released. Similar performance may be demonstrated for films made from such betaine esters and a copolymer based on dimethylaminoethyl methacrylate, butyl methacrylate, and methyl methacrylate when exposing such films to first neutral aqueous solutions, and then to slightly acidic solutions (pH 5.5).

By using a composition having encapsulation material that is triggered by a specific change in the environment, such as for example, contact with vaginal fluids that might be excreted from a user with a vaginal infection, or for contact with other basic or slightly basic environments, the first stage trigger can be activated, thereby freeing up potential access to the second stage trigger of the betaine ester or betaine ester derivative. For example, particular ailments may raise the pH level of vaginal secretions from a normally acidic level to a neutral or slightly alkaline level. Under normal conditions in which pH of such secretions is acidic, such encapsulation chemistry would not be triggered. However, once vaginal fluid of a neutral or slightly alkaline level is introduced to the encapsulation chemistry triggered by a neutral or slightly alkaline environment, the encapsulation chemistry would allow for the release of betaine esters or betaine ester derivatives. Upon continued contact of the betaine esters or betaine ester derivatives with an aqueous medium, the functional active on the betaine ester would be released.

Examples of various encapsulation chemistries useful in the invention are illustrated below.

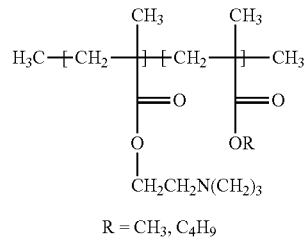

EUDRAGIT E-100

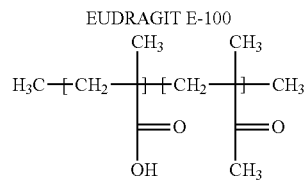

EUDRAGIT S-100

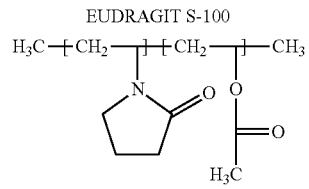

Vinylpyrrolidone/vinyl acetate copolymers

Desirably, for the purposes of this application, the amount of encapsulation chemistry present in the composition is between about 20 and 99.9% by weight. Alternatively, such encapsulation chemistry is present in the composition is between about 40 and 90% by weight. Still in a further alternative embodiment, such encapsulation chemistry is present in the composition in an amount of between about 60 and 95% by weight.

Other Chemical Components of Triggerable Composition

The triggerable composition may also contain other components such as solvents, plasticizers, surfactants or wettability agents, pH adjusters and viscosity enhancers. Based on the substrate or surface on which the composition is to be deposited, or the lotion, cream or medicament that the composition is to be used in, the composition may require addition of other ingredients to immobilize or adhere the encapsulation and betaine ester components more securely to the substrate, or in the formulation. The composition may also contain water-miscible or hydrophilic polymers. Furthermore, the composition may also contain other additives to adjust surface tension, or other physical and chemical properties. Alternatively, the substrates can be treated with different materials to modify their surface properties before the deposition of the composition, to improve the adhesion of the composition. The wettability enhancing agent can be a single surfactant or a mixture of surfactants. The surfactants can be non-ionic, neutral surfactants, or ionic surfactants. The ionic surfactants can be either positively charged or negatively charged. Examples of non-ionic surfactants include alkyl poly(ethylene oxide) such as copolymers of poly(ethylene oxide) and poly(propylene oxide) (commercially called Poloxamers or Poloxamines), alkyl polyglucosides such as octylglucoside and decyl maltoside, fatty alcohols such as cetyl alcohol, oleyl alcohol, cocamide MEA and cocamide DEA. Examples of ionic surfactants include anionic (e.g., based on sulfate, sulfonate or carboxylate anions) surfactants such ass (SDS), ammonium lauryl sulfate and other alkyl sulfate salts, Sodium laureth sulfate, also known as sodium lauryl ether sulfate (SLES), Alkyl benzene sulfonate, soaps or fatty acid salts; and cationic (e.g., based on quaternary ammonium cations) surfactants such as Cetyl trimethylammonium bromide (CTAB) a.k.a. hexadecyl trimethyl ammonium bromide, and other alkyl trimethyl ammonium salts, Cetyl pyridinium chloride (CPC), Polyethoxylated tallow amine (POEA), Benzalkonium chloride (BAC), Benzethonium chloride (BZT); or Zwitterionic (amphoteric) surfactants such as Dodecyl betaine, Dodecyl dimethyl amine oxide, Cocamidopropyl betaine, Coco ampho glycinate. Alternatively, the wettability enhancing agents may also be hydrophilic molecules. The hydrophilic molecules may also be polymers such as polyethylene glycol and its copolymers.

The triggerable composition of the invention may be applied to a substrate such as an absorbent article, or layer within an absorbent article, by any number of known applications or printing techniques. For example, the triggerable composition of the present invention may be deposited on a substrate by various surface deposition or printing methods such as brushing, flexographic printing, gravure roll printing, stamping, screen print, spraying techniques, dip and squeeze, and digital print methods. Further, the composition may be applied in a melt form and allowed to solidify on a treated substrate. As also noted, the composition may be part of a lotion, cream or medicament as well.

Placement of the triggerable composition can be on any number of substrates. The substrate sheets can for instance, include nonwoven or woven sheets. Such sheets can include synthetic or natural fibrous materials such as for example, extruded spunbond, and meltblown webs, bonded carded webs, or airlaid materials, spun cellulosic, wool or synthetic yarns. Such sheets may further include cellulosic-based dry or wet laid tissue or paper sheets. Additionally, such substrates may include film or foam sheets, laminates of film, foam and fibrous layers, or laminates of multiple fibrous, film and foam layers. Such substrates/sheets may be placed as layers within medical or beauty care articles, personal care hygienic articles such as absorbent articles, or may themselves serve as the absorbent article such as as a towel, tissue or wipe. Further, such triggerable composition can be used as components in lotions, creams and medicaments, such as tablets or suppositories.

Placement of such composition in an article/absorbent article may be across the entire article's longitudinal and transverse or lateral (width) dimensions, or layer of an article, or alternatively, may be limited to certain locations within the article, or layer(s) on the article. For example, such composition may be placed at a location specifically designed to contact aqueous-based waste, such as a highly probable "soiling area" in an article's or layer's central crotch region. Such treated layers may include the topsheet layer, backsheet layer (inner surface) or absorbent core layer. Other interior positioned layers may also be treated with the coating composition. In an alternative embodiment, if a relatively hydrophobic betaine ester is selected for the composition (or one having relatively hydrophobic R3-R5 groups), it may be desirable to limit the placement of the coating formulation to certain locations on an absorbent article that would not directly impact the absorbency pathways of an article, such as on an inside surface of a backsheet layer (as opposed to a topsheet layer or absorbent core layer), or side areas of a topsheet layer, absorbent core layer or other interior situated layer.

EXAMPLES

The following components were blended together to form coating compositions for the purpose of demonstrating the effectiveness of using a two stage triggerable composition, including an encapsulated betaine ester with functional active, according to the present disclosure.

Example 1

To 3 ml of EUDRAGIT S100 (100 mg/ml) from Degussa in ethanol, was added 15 mg betaine eugenol ester dissolved in 0.25 ml methanol, to formulate a coating solution. The solution was brushed on a 24 cm by 45 cm piece of polypropylene film and air-dried overnight. No eugenol smell was detected. When a piece of the coated film was exposed to water having a pH of approximately 6.8 no eugenol smell was detected. However, a steady release of eugenol smell was detected when a piece of the coated film was wetted with an aqueous solution of sodium bicarbonate having a pH of approximately 8.5 was exposed contacted with the film.

Example 2

To 3 ml EUDRAGIT S100 (100 mg/ml) in ethanol was added 15 mg eugenol dissolved in 0.25 ml methanol to make a coating solution. The solution was brushed on a 24 cm by 45 cm piece of polypropylene film and air-dried overnight. A slight eugenol smell was detected. When a piece of the coated film was exposed to water at approximately pH 6.8, some eugenol smell was detected. However a burst release of eugenol smell was detected when a piece of the coated film was wetted with an aqueous solution sodium bicarbonate having a pH of approximately 8.5.

Example 3

To 3 ml EUDRAGIT E100 (100 mg/ml) From Degussa in ethanol was added 15 mg betaine eugenol ester dissolved in 0.25 ml methanol to make a coating solution. The solution was brushed on a 24 cm by 45 cm piece of polypropylene film and air-dried overnight. No eugenol smell was detected. When a piece of the coated film was exposed to water at approximately a pH of 6.8, no eugenol smell was detected. However, a steady release of eugenol smell was detected when a piece of the coated film was wetted with an aqueous solution of hydrogen chloride, having a pH of approximately 5.5.

Example 4

To 3 ml of EUDRAGIT E100 (100 mg/ml) in ethanol was added 15 mg Eugenol dissolved in 0.25 ml methanol to make a coating solution. The solution was brushed on a 24 cm by 45 cm piece of polypropyl ene film and air-dried overnight. A slight eugenol smell was detected. When a piece of the coated film was exposed to water of approximately 6.8 pH, some eugenol smell was detected. However, a burst release of eugenol smell was detected when a piece of the coated film was wetted with an aqueous solution of hydrogen chloride having a pH of approximately 5.5.

Example 5

To 3 ml of PVP/VA I-335 from ISP (100 mg/ml) in ethanol was added 15 mg betaine eugenol ester dissolved in 0.25 ml methanol to make a coating solution. The solution was brushed on a 24 cm by 45 cm piece of polypropylene film and air-dried overnight. No eugenol smell was detected. When a piece of the coated film was exposed to water having a pH of approximately 6.8, a steady release of eugenol smell was detected Example 6

To 3 ml PVP/VA I-335 (100 mg/ml) was added 15 mg eugenol dissolved in 0.25 ml methanol to make a coating solution. The solution was brushed on a 24 cm by 45 cm piece of polypropyl ene film and air-dried overnight. A slight eugenol smell was detected. When a piece of the coated film was exposed to water having a pH of approximately 6.8, a burst release of eugenol smell was detected.

Figure 2:
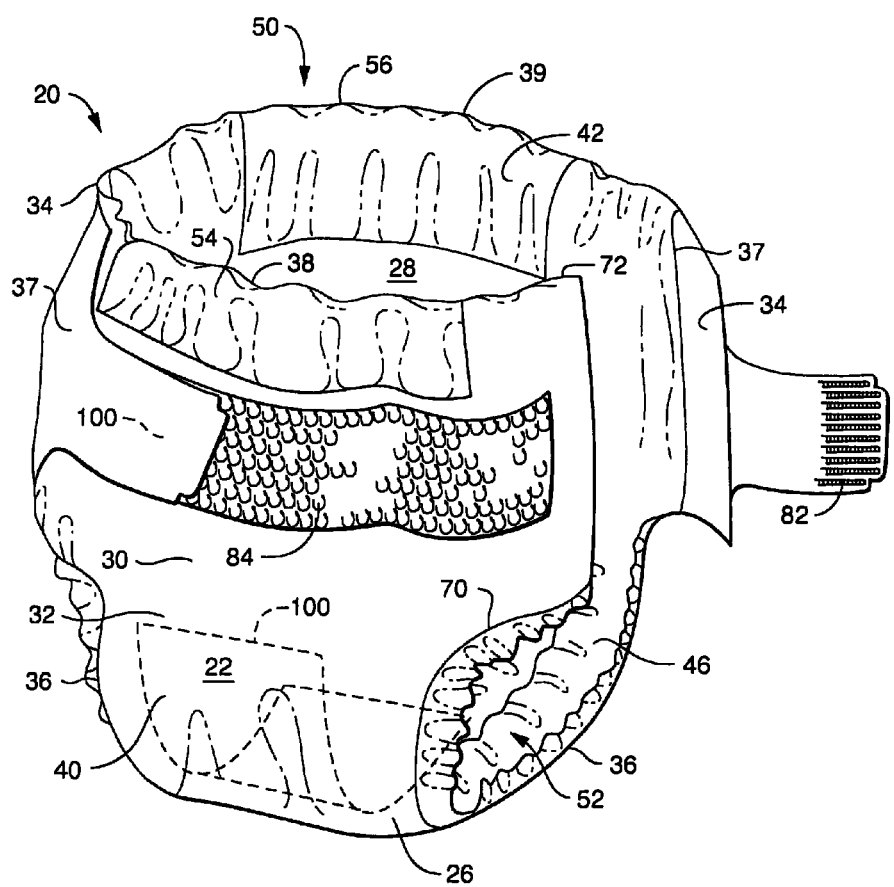
FIG. 2 is a front perspective view of the diaper embodiment illustrated in FIG. 1.

Referring to FIGS. 1 and 2, for exemplary purposes, an absorbent article 20 in the form of a diaper that may be made in accordance with the present disclosure is shown. The absorbent article 20 may or may not be disposable. It is understood that the present disclosure is suitable for use with various other absorbent articles intended for personal wear, including but not limited to diapers, training pants, swim pants, feminine hygiene products, incontinence products, medical garments, surgical pads and bandages (as shown particularly in FIG. 5), other personal care or health care products such as gowns and sterilization wraps, and the like without departing from the scope of the present invention.

By way of illustration only, various materials and methods for constructing absorbent articles such as the article 20 of the various aspects of the present invention are disclosed in PCT Patent Application WO 00/37009 by Fletcher et al; U.S. Pat. No. 4,940,464 to Van Gompel et al.; U.S. Pat. No. 5,766,389 to Brandon et al., and U.S. Pat. No. 6,645,190 to Olson et al. which are incorporated herein by reference in their entirety.

Figure 3:
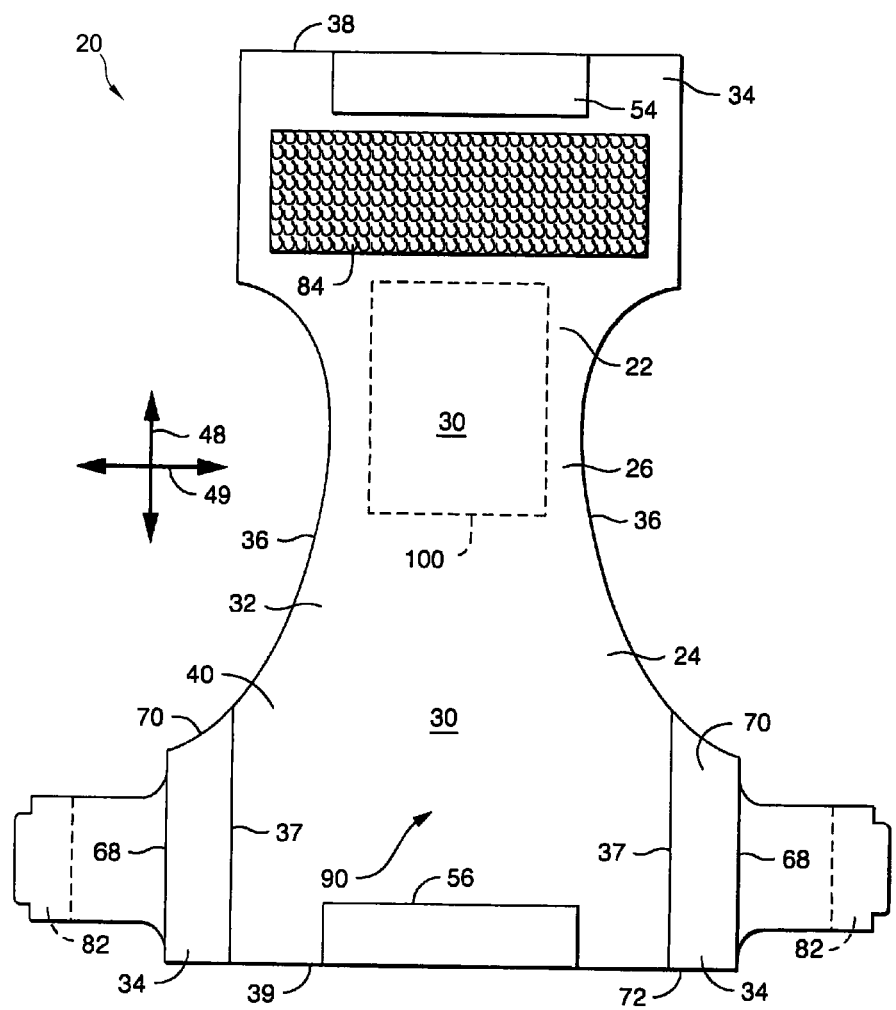
FIG. 3 is a plan view of the diaper embodiment shown in FIG. 1 with the diaper in an unfastened, unfolded and laid flat condition showing the surface of the article that faces away from the wearer (garment facing side).
Figure 4:
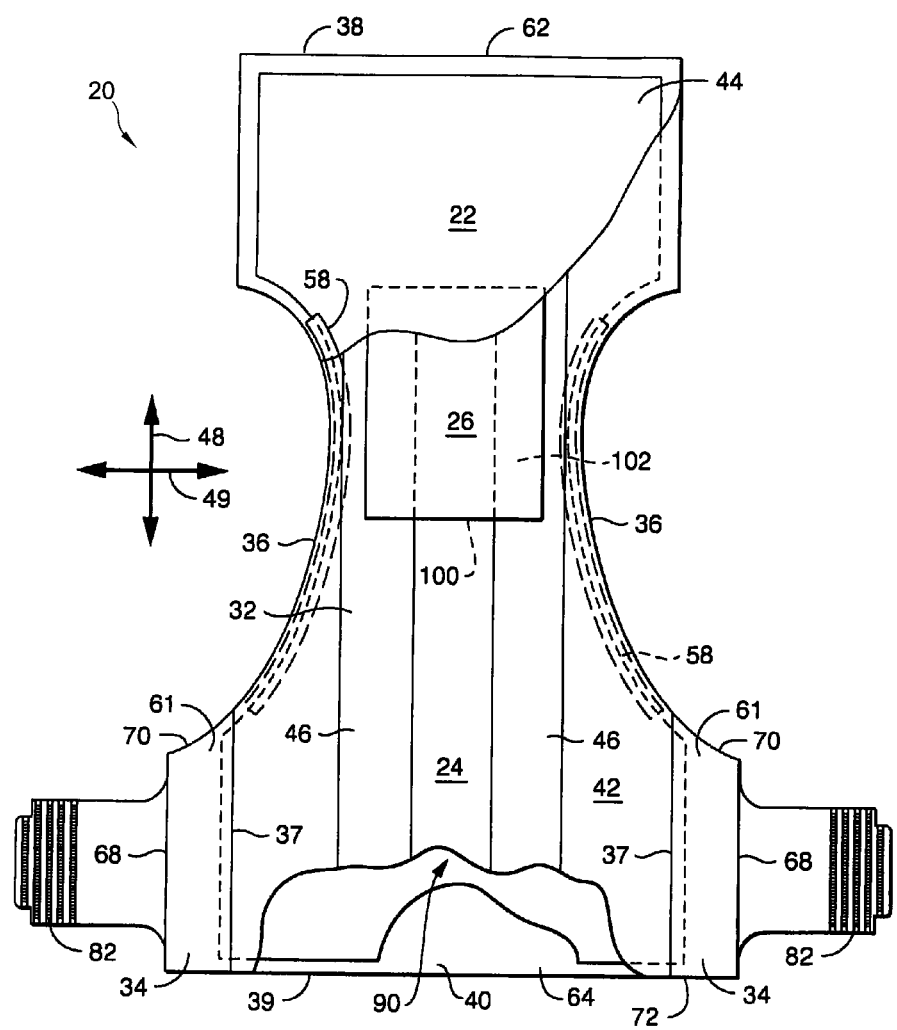
FIG. 4 is a cut-away plan view of an alternative embodiment of the diaper absorbent article shown in FIG. 3, which shows the surface of the article that faces the wearer skin when worn.

An absorbent article 20 is representatively illustrated in FIG. 1 in a partially fastened condition. The absorbent article 20 shown in FIGS. 1 and 2 is also represented in FIGS. 3 and 4 in an opened and unfolded state. Specifically, FIG. 3 is a plan view illustrating the exterior side of the absorbent article 20, while FIG. 4 illustrates the interior side of an alternative embodiment of the absorbent article 20. As shown in FIGS. 3 and 4, the absorbent article 20 defines a longitudinal direction 48 that extends from the front of the article when worn to the back of the article. Opposite to the longitudinal direction 48 is a lateral (or transverse) direction 49.

The absorbent article 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The absorbent article 20 also defines an inner surface 28 adapted in use (e.g., positioned relative to the other components of the article 20) to be disposed toward the wearer, and an outer surface 30 opposite the inner surface. The front and back regions 22, 24 are those portions of the absorbent article 20, which when worn, wholly or partially cover or encircle the waist or mid-lower torso of the wearer. The crotch region 26 generally is that portion of the absorbent article 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated absorbent article 20 includes a chassis 32 that, in this embodiment, encompasses the front region 22, the back region 24, and the crotch region 26. Referring to FIGS. 1-4, the chassis 32 includes an outer cover 40 and a bodyside liner 42 (FIGS. 1 and 4) that may be joined to the outer cover 40 in a superimposed relation therewith by adhesives, ultrasonic bonds, thermal bonds or other conventional techniques. Referring to FIG. 4, the liner 42 may suitably be joined to the outer cover 40 along the perimeter of the chassis 32 to form a front waist seam 62 and a back waist seam 64. As shown in FIG. 4, the liner 42 may suitably be joined to the outer cover 40 to form a pair of side seams 61 in the front region 22 and the back region 24. The liner 42 can be generally adapted, i.e., positioned relative to the other components of the article 20, to be disposed toward the wearer's skin during wear of the absorbent article. The chassis 32 may further include an absorbent structure 44 particularly shown in FIG. 4 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

The elasticized containment flaps 46 as shown in FIG. 4 define a partially unattached edge which assumes an upright configuration in at least the crotch region 26 of the absorbent article 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 to Enloe, which is incorporated herein by reference.

To further enhance containment and/or absorption of body exudates, the absorbent article 20 may also suitably include leg elastic members 58 (FIG. 4), as are known to those skilled in the art. The leg elastic members 58 can be operatively joined to the outer cover 40 and/or the bodyside liner 42 and positioned in the crotch region 26 of the absorbent article 20.

The leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retroactive forces are imparted to the substrate. In one particular aspect, for example, the leg elastic members 58 may include a plurality of dry-spun coalesced multifilament spandex elastomeric threads sold under the trade name LYCRA.

In some embodiments, the absorbent article 20 may further include a surge management layer (not shown) which may be optionally located adjacent the absorbent structure 44 and attached to various components in the article 20 such as the absorbent structure 44 or the bodyside liner 42 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein.

As shown in FIGS. 1-4, the absorbent article 20 further includes a pair of opposing elastic side panels 34 that are attached to the back region of the chassis 32. As shown particularly in FIGS. 1 and 2, the side panels 34 may be stretched around the waist and/or hips of a wearer in order to secure the garment in place. As shown in FIGS. 3 and 4, the elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative embodiment, the elastic side panels may also be integrally formed with the chassis 32. For instance, the side panels 34 may comprise an extension of the bodyside liner 42, of the outer cover 40, or of both the bodyside liner 42 and the outer cover 40.

In the embodiments shown in the figures, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIGS. 1 and 2, the elastic side panels 34 may be connected by a fastening system 80 to define a 3-dimensional diaper configuration having a waist opening 50 and a pair of leg openings 52. The waist opening 50 of the article 20 is defined by the waist edges 38 and 39 which encircle the waist of the wearer.

In the embodiments shown in the figures, the side panels are releasably attachable to the front region 22 of the article 20 by the fastening system. It should be understood, however, that in other embodiments the side panels may be permanently joined to the chassis 32 at each end. The side panels may be permanently bonded together, for instance, when forming a training pant or absorbent swimwear.

The elastic side panels 34 each have a longitudinal outer edge 68, a leg end edge 70 disposed toward the longitudinal center of the absorbent article 20, and waist end edges 72 disposed toward a longitudinal end of the absorbent article. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present invention. As shown in FIG. 4, the outer edges 68 are generally parallel to the longitudinal direction 48 while the waist end edges 72 are generally parallel to the transverse/lateral axis 49. It should be understood, however, that in other embodiments the outer edges 68 and/or the waist edges 72 may be slanted or curved as desired. Ultimately, the side panels 34 are generally aligned with a waist region 90 of the chassis.

The fastening system 80 may include laterally opposite first fastening components 82 adapted for refastenable engagement to corresponding second fastening components 84. In the embodiment shown in the figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 may be any mating and/or engaging refastenable fasteners suitable for absorbent articles, such as adhesive fasteners, cohesive fasteners, mechanical fasteners, a combination of such, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners. Alternatively, the first fastening components 82 may include loop fasteners and the second fastening components 84 may be complementary hook fasteners. In another aspect, the fastening components 82, 84 can be interlocking similar surface fasteners, or adhesive and cohesive fastening elements such as an adhesive fastener and an adhesive receptive landing zone or material; or the like. One skilled in the art will recognize that the shape, density and polymer composition of the hooks and loops may be selected to obtain the desired level of engagement between the fastening components 82, 84. Suitable fastening systems are also disclosed in the previously incorporated PCT Patent Application WO 00/37009 by Fletcher et al. and the previously incorporated U.S. Pat. No. 6,645,190 to Olson et al.

In the embodiment shown in the figures, the fastening components 82 are attached to the side panels 34 along the edges 68. In this embodiment, the fastening components 82 are not elastic or extendable. In other embodiments, however, the fastening components may be integral with the side panels 34. For example, the fastening components may be directly attached to the side panels 34 on a surface thereof.

In addition to possibly having elastic side panels, the absorbent article 20 may include various waist elastic members for providing elasticity around the waist opening. For example, as shown in the figures, the absorbent article 20 can include a front waist elastic member 54 and/or a back waist elastic member 56.

As described above, the present disclosure is directed to incorporating a two-stage triggerable composition into the absorbent article 20. In particular, the composition is placed on a layer within the article configured to release ascent, antibacterial agent, skin repairing agent, antioxidant agent or other functional active when exposed to a first environmental stimulus followed by contact with an aqueous medium, such as contact with a body fluid, such as urine, menses, vaginal secretions, sweat, mucous, or a loose bowel movement. In one embodiment, for instance, the composition is coated as a patch 100 on an individual layer within the diaper, which will come in contact with an aqueous medium following contact with an initial environmental stimulus. The coated composition for example, may be coated on a portion of the topsheet layer (user facing surface or garment facing surface), the absorbent core layer (or other internal article layer), or on the inside surface of the backsheet layer. Alternatively, such coating composition may be placed on a discrete patch of separate material 100 that functions as a carrier layer, such as for example a nonwoven material (as seen in the alternative embodiment of FIG. 4), which includes a user facing surface 102, for releasing the coating composition upon triggering by an environmental stimulus and contact with an aqueous medium. The two stage triggerable composition may also be made to be in particulate form and mixed with superabsorbent materials or other absorbent components as a part of the absorbent layer.

Figure 5:
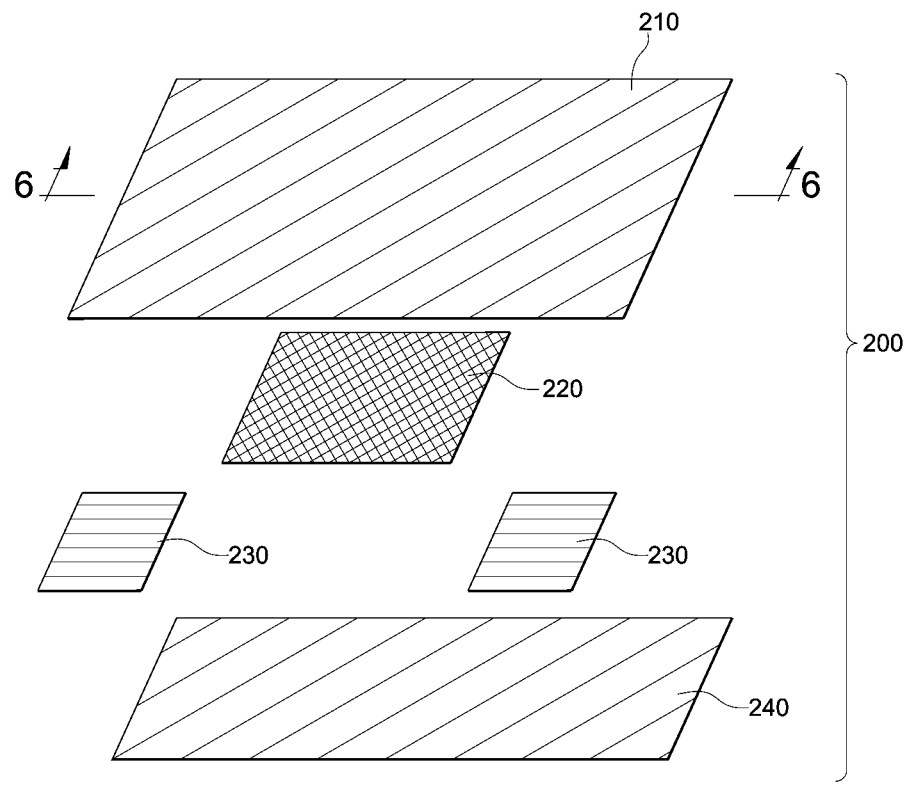
FIG. 5 is an exploded perspective view of an absorbent article in the form of a bandage, including the composition of the invention.
Figure 6:
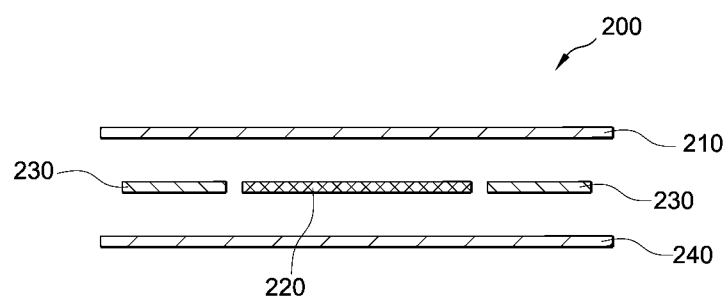
FIG. 6 is a cross-sectional view of FIG. 5 taken along line 6-6.

As can be seen in FIG. 5, which shows an exploded view of a bandage 200 in accordance with the invention, such bandage desirably includes a liquid impermeable, but breathable layer 210. Such layer may be made for example from a polymeric film, foam, or liquid impermeable fibrous nonwoven material. At least one patch 230, but desirably two patches, of pressure sensitive adhesive are affixed to the surface of the layer 210 for adhering the liquid impermeable layer to the surface of a user's skin. Desirably a composition-releasing layer 220, which has been coated with a composition of the present invention is positioned on the layer 210 for releasing such coating to a user's skin, upon triggering by environmental stimuli. Such composition-releasing layer 220 can be constructed from any number of materials, such as for example an absorbent fibrous material, foam material, or laminate of multiple materials. Such absorbent fibrous material may be from a nonwoven or woven material. Such nonwoven materials include extruded or carded nonwoven webs or airlaid materials, such as spunbond, meltblown, or through-air bonded carded webs, or laminates thereof. Alternatively, such material may be a cellulosic-based material such as an airlaid or wetlaid tissue-like material. In a further alternative, such material may be a foam sheet, such as an open or closed cell foam that has been coated or treated with the inventive composition. A release sheet 240, for protecting the coating composition and adhesive is desirably affixed over the adhesive patches and composition-releasing layer. Such a bandage construction can be seen in cross-sectional view in FIG. 6.

As can be seen, controlled release of chemical actives can be achieved in a two-stage process, by utilizing a stimulus sensitive encapsulation chemistry and aqueous medium sensitive betaine ester chemistry in a single composition. Such a composition relies on two different triggering stimuli (such as pH and aqueous medium contact or enzyme and aqueous medium contact) to release an active chemistry, thereby providing stability to functional actives, and control in the graduated release of such actives to the environment or a desired location.

The present invention has been described in general and in detail by means of examples. Persons of skill in the art understand that the invention is not limited necessarily to the embodiments specifically disclosed, but that modifications and variations may be made without departing from the scope of the invention as defined by the following claims or their equivalents.

I claim:

1. A triggerable composition for two-stage, controlled release of a functional active chemical comprising:
    a betaine ester or betaine ester derivative of a functional active with at least one hydroxyl group that releases the functional active through a hydrolysis reaction upon contact with an aqueous medium, wherein the betaine ester or betaine ester derivative is configured to undergo the hydrolysis reaction in a basic aqueous medium, a neutral aqueous medium, and an acidic aqueous medium, and wherein the betaine ester or betaine ester derivative is not part of a larger polymer structure and not itself bonded as a functional group to a chain base structure, and
    an encapsulation material for encapsulating the betaine ester or betaine ester derivative including a functional active, the encapsulation material triggerable to release the betaine ester or betaine ester derivative upon the occurrence of an environmental stimulus.

2. The triggerable composition of claim 1 wherein said stimulus is selected from the group consisting of a pH change, an enzymatic change, a temperature change, an ion concentration change, and a ligand concentration change.

3. The triggerable composition of claim 1 wherein said stimulus is selected from the group consisting of a pH change, an enzymatic change and a temperature change.

4. The triggerable composition of claim 1 wherein said composition is in a form of particles, microparticles, nanoparticles, fibers, sheet, films or a combination thereof.

5. The triggerable composition of claim 1, wherein said encapsulation material is triggerable to release a betaine ester or betaine ester derivative upon the occurrence of a pH change.

6. The triggerable composition of claim 1, wherein said encapsulation material is selected from copolymers of methacrylic acid and methyl methacrylate which are sensitive to basic aqueous solutions, copolymers of dimethylaminoethyl methacrylate, butyl methacrylate, and methyl methacrylate which are sensitive to acidic aqueous solutions, and vinylpyrrolidone/vinyl acetate copolymers which are sensitive to neutral aqueous solutions.

7. The triggerable composition of claim 1, wherein said functional active is selected from the group consisting of a fragrance, an antimicrobial agent, an antioxidant agent, a skin repairing agent, an antifungal agent, a hormone, and a medically active agent.

8. The triggerable composition of claim 7, wherein said functional active is a fragrance having at least one hydroxyl group, selected from the group consisting of thymol, eugenol, menthol, vanillin or combinations thereof.

9. The triggerable composition of claim 7, wherein said functional active is a skin repairing agent.

10. The triggerable composition of claim 9, wherein said skin repairing agent is derived from retinol.

11. An absorbent article including at least one absorbent layer, said absorbent article including the triggerable composition of claim 1.

12. The absorbent article of claim 11 including a topsheet layer, a backsheet layer, and at least one absorbent core layer, wherein said triggerable composition is included with at least one of said topsheet layer, absorbent core layer and said backsheet layer.

13. The absorbent article of claim 11 further including a carrier layer, wherein said triggerable composition is included with said carrier layer for carrying the triggerable composition within said absorbent article.

14. The absorbent article of claim 11, wherein said absorbent article is selected from the group consisting of feminine care hygiene articles, adult incontinence articles, baby and child care articles, bandages, medical garments and skin treatment sheets.

15. The triggerable composition of claim 1 being a part of a lotion, cream or medicament.

16. A triggerable composition for two-stage, controlled release of a functional active chemicals comprising:

a betaine ester or betaine ester derivative for release of a functional active contained on the betaine ester or betaine ester derivative, through a hydrolysis reaction upon contact with an aqueous medium, wherein the betaine ester or betaine ester derivative is configured to undergo the hydrolysis reaction in a basic aqueous medium, a neutral aqueous medium, and an acidic aqueous medium, and wherein the betaine ester or betaine ester derivative is not part of a larger polymer structure and not itself bonded as a functional group to a chain base structure, and an encapsulation material for encapsulating the betaine ester or betaine ester derivative including a functional active, the encapsulation material triggerable to release the betaine ester or betaine ester derivative upon the occurrence of an environmental stimulus, wherein said environmental stimulus is a pH change.

17. The composition of claim 16 wherein said stimulus is a pH change from an acidic to neutral or basic environment, and said encapsulation material is selected from the group consisting of copolymers of methacrylic acid and methyl methacrylate which are sensitive to basic aqueous solutions, and vinylpyrrolidone/vinyl acetate copolymers which are sensitive to neutral aqueous solutions.

18. The composition of claim 16 wherein said stimulus is a pH change from a basic to neutral or acidic environment, and said encapsulation material is selected from the group consisting of copolymers of dimethylaminoethyl methacrylate, butyl methacrylate, and methyl methacrylate which are sensitive to acidic aqueous solutions, and vinylpyrrolidone/vinyl acetate copolymers which are sensitive to neutral aqueous solutions.

19. The composition of claim 16 wherein said functional active is a fragrance.

20. The composition of claim 19 wherein said fragrance is selected from thymol, menthol and eugenol.

* * * * *